United States Patent [19]  [11] Patent Number: 4,596,596
Simmons et al.  [45] Date of Patent: Jun. 24, 1986

[54] 1-,2-,AND 3-N,N-DIALKYLCARBAMYL-1-H-1,2,3-TRIAZOLES

[75] Inventors: Kirk A. Simmons, Langhorne, Pa.; Andrea Leone-Bay, Ridgefield, Conn.

[73] Assignee: Stauffer Chemical Company, Westport, Conn.

[21] Appl. No.: 747,464

[22] Filed: Jun. 21, 1985

[51] Int. Cl.$^4$ .............. A01N 43/647; C07D 249/04; C07D 249/06; C07D 401/06; C07D 403/06
[52] U.S. Cl. .................................. 71/92; 546/210; 548/255
[58] Field of Search .............. 546/210; 548/255; 71/92

[56] References Cited
U.S. PATENT DOCUMENTS
4,233,059 11/1980 Krüger et al. ............... 548/255

Primary Examiner—Robert T. Bond
Attorney, Agent, or Firm—Edwin H. Baker

[57] ABSTRACT

A compound having the structural formula

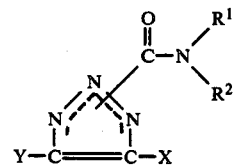

wherein X is hydrogen or bromine; Y is bromine, phenyl, $C_1$–$C_4$ alkyl or $C_4$–$C_6$ cycloalkyl; $R^1$ and $R^2$ independently are $C_1$–$C_6$ alkyl or $R^1$ and $R^2$ together form a ring with the nitrogen to which they are attached having 3–8 carbon atoms, optionally substituted with one or two methyl groups.

20 Claims, No Drawings

1-,2-,AND 3-N,N-DIALKYLCARBAMYL-1-H-1,2,3-TRIAZOLES

BACKGROUND OF THE INVENTION

Compounds of the formula shown below wherein R is 2-benzothiazolyl,

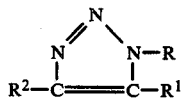

2-benzimidazolyl, 2-benzoxazolyl, s-triazinyl or 4-pyrimidinyl and $R^1$ and $R^2$ are hydrogen, hydroxyalkyl, carbomethoxy, alkyl, $(CH_2)_3$, $(CH_2)_4$, or $(CH_2)_5$ are described by Auderhaar and Meyer in Ger. Offen. No. 2,263,878 as being pesticidal.

DESCRIPTION OF THE INVENTION

This invention relates to of 1-, 2- and 3-N,N-dialkylcarbamyl-1-H-1,2,3-triazoles as herbicides. The novel compounds of this invention have the following structural formula (A)

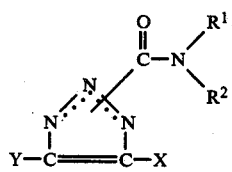

wherein X is hydrogen or bromine, preferably bromine; Y is bromine, phenyl, $C_1$-$C_4$ alkyl or $C_4$-$C_6$ cycloalkyl, preferably bromine; most preferably both X and Y are bromine; $R^1$ and $R^2$ independently are $C_1$-$C_6$ alkyl, preferably $C_1$-$C_4$ alkyl, $C_1$-$C_4$ alkoxy, preferably $C_1$-$C_2$ alkoxy, aryl, or $R^1$ and $R^2$ together form a ring with the nitrogen to which they are attached, having 3-8 carbon atoms, preferably $C_4$-$C_6$ carbon atoms, optionally substituted with one or two methyl groups.

Structural formula A is intended to define compounds of either of the following three structural isomers:

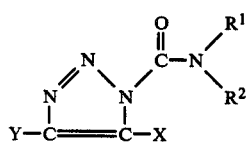
3-isomer

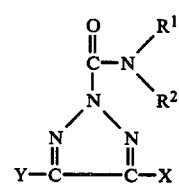
2-isomer

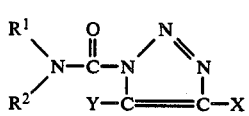
1-isomer or mixtures of the three isomers in any proportion.
All three isomers are herbicidally active.

In the above description of the compounds of this invention alkyl includes both straight and branched configurations; for example, methyl, ethyl, n-propyl, isopropyl, n-butyl, sec-butyl, isobutyl, and tert-butyl, the amyls, the hexyls, the heptyls, the nonyls and the decyls.

The compounds of this invention are active herbicides of a general type. That is, they are herbicidally effective against a wide range of plant species. The method of controlling undesirable vegetation of the present invention comprises applying an herbicidally effective amount of the above-described compounds to the area where control is desired.

The compounds of the present invention can be prepared by the following general method.

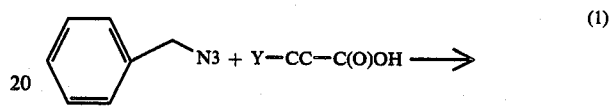
(1)

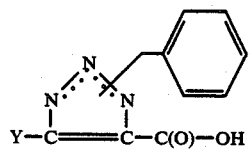

wherein Y is as defined except bromine.

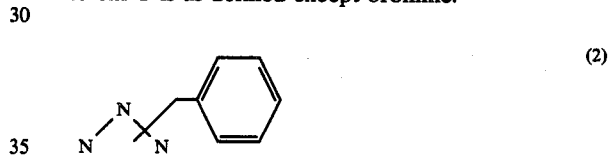
(2)

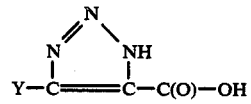

wherein Y is as defined except bromine.

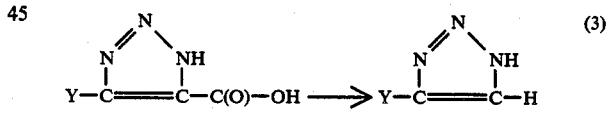
(3)

wherein Y is as defined except bromine.

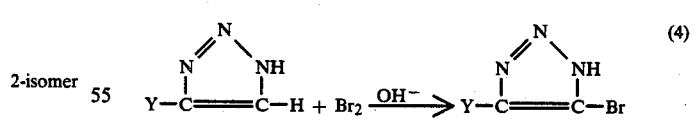
(4)

wherein Y is as defined except bromine.

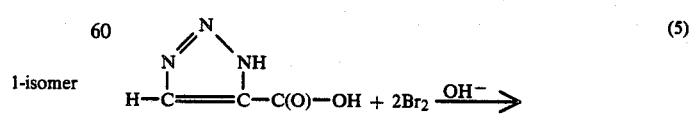
(5)

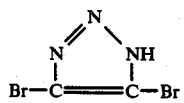

-continued

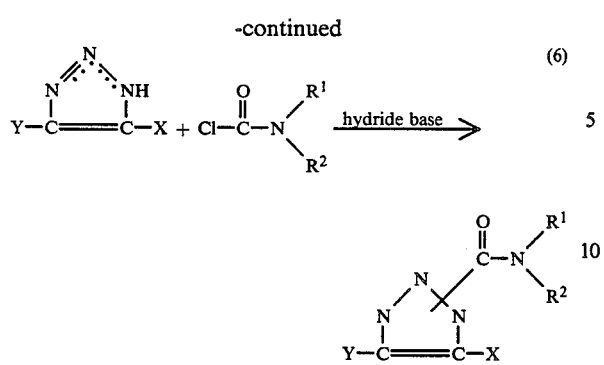

wherein X, Y, R¹ and R² are as defined.

Generally step (1) is run in a solvent such as acetone, at a temperature of about 25° to 100° C. using equimolar amounts of the two reactants.

Reaction step (2) is run in liquid ammonium at −78° C. with a mole amount of sodium metal. If water is present, an excess of ammonia should be used.

Reaction step (3) is carried out at the melting temperature of the reactant, usually at about 150°–250° C.

Reaction step (4) is run in a solvent such as water using 2 to 3 equivalents of a base, preferably sodium hydroxide. The halogen, preferably bromine, is used in an amount equimolar to the triazole reactant.

Reaction step (5) is run in a solvent such as water using 2 to 3 equivalents of a base, preferably sodium carbonate. The halogen, preferably bromine, is used in an amount twice the equimolar to the triazole reactant.

Reaction step (6) is run in an organic solvent such as tetrahydrofuran, at a temperature of about 25°–100° C., preferably reflux temperature, using equal mole amounts of the three reactants and a hydride base. Preferably, the hydride base is sodium hydride. Organic bases can also be use.

The reaction product is a mixture of (1), (2) and (3) isomers and is worked up by conventional techniques.

The following examples teach the synthesis of representative compounds of this invention.

EXAMPLE 1

1(2 or 3)-Benzyl-1H-1,2,3-triazole-4-carboxylic acid

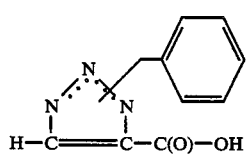

To a solution of 84 milliliters (ml) of acetone and 35.8 grams (g) (269 mmoles) of benzyl azide, 19.3 g (276 mmoles) of propiolic acid was added by drop. The reaction mixture was stirred and heated to reflux overnight. After cooling to 0° C., 33.6 g (62%) of 1(2 or 3)-benzyl-1H-1,2,3-triazole-4-carboxylic acid precipitated from the reaction solution as white crystals. The structure was confirmed by nuclear magnetic resonance (n.m.r.) and infrared spectroscopy (I.R.).

EXAMPLE 2

1H-1,2,3-triazole-4-carboxylic acid

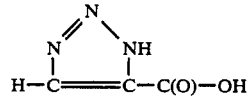

To a mixture of 33 g (163 mmoles) of 1(2 or 3)-benzyl-1H-1,2,3-triazole-4-carboxylic acid in 350 ml of liquid ammonium at −78° C., 10.9 g (474 mmoles) of sodium pellets were added, in portions, until the solution maintained a dark blue color. The reaction was then quenched with 11 g (141 mmoles) of ammonium bicarbonate. The resulting yellow mixture was allowed to come to room temperature and the ammonia evaporated. The solid residue was dissolved in 80 ml of water and extracted with ether. The aqueous layer was then adjusted to pH 1 with 12N hydrochloric acid and 16.4 (100%) of 1H-1,2,3-triazole-4-carboxylic acid precipitated as a white solid. The structure was confirmed by n.m.r. and I.R.

EXAMPLE 3

4,5-Dibromo-1H-1,2,3-triazole

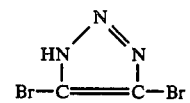

To a solution of 140 g (1.32 moles) of sodium carbonate in 650 ml of water was added 75 g (661 mmoles) of 1H-1,2,3-triazole-4-carboxylic acid. The resulting solution was subjected to the dropwise addition of 208 g (1322 mmoles) of bromine and then stirred overnight at room temperature. After cooling to 0° C., the reaction was adjusted to pH 4 with 12N hydrochloric acid causing precipitation of 147 g (98%) of 4,5-dibromo-1-H1,2,3-triazole as a white solid. The structure was confirmed by n.m.r. and I.R.

EXAMPLE 4

1(2 or 3)-N,N-Diethylcarbamyl-4,5-dibromo-1H-1,2,3-triazole

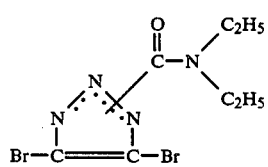

To a suspension of 213 milligrams (mg) (8.89 mmoles) of sodium hydride in 20 ml of anhydrous tetrahydrofuran was added 2 g (8.89 mmoles) of 4,5-dibromo-1H-1,2,3-triazole. The resulting suspension was cooled to 0° C. and 1.2 g (8.89 moles) of N,N-diethylcarbamoyl chloride was added by drop. The reaction mixture was heated to reflux overnight and the precipitated sodium chloride was removed by filtration. Concentration of the filtrate in vacuo gave 2.4 g (82%) of 1(2 or 3)-N,N-diethylcarbamyl-4,5-dibromo-1H-1,2,3-triazole as a yellow oil. The structure was confirmed by n.m.r. and I.R.

EXAMPLE 5

1(2 or 3)-Benzyl-5-ethyl-1H-1,2,3-triazole-4-carboxylic acid

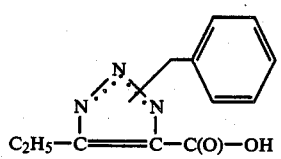

To a solution of 4.3 g (187 mmoles) of sodium pellets in 80 ml of absolute ethanol under nitrogen was added 18.0 g (125 mmoles) of ethyl propionylacetate followed by 16.6 g (125 mmoles) of benzyl azide. The resulting reaction mixture was stirred under reflux for two days. Upon cooling to room temperature, 45 ml of 4M aqueous sodium hydroxide was added dropwise and the mixture was refluxed for 3 hours. The reaction was again cooled to room temperature and concentration in vacuo gave a gummy solid. This residue was dissolved in 125 ml of water and extracted with ether. Acidification (pH 1) with 12N hydrochloric acid caused precipitation of 25.1 g (87%) of 1(2 or 3)-benzyl-5-ethyl-1H-1,2,3-triazole-4-carboxylic acid as a tan solid. The structure was confirmed by n.m.r. and I.R.

EXAMPLE 6

5-Ethyl-1H-1,2,3-triazole-4-carboxylic acid

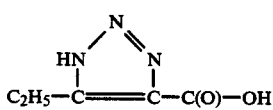

To a mixture of 24 g (104 mmoles) of 1(2 or 3)-benzyl-5-ethyl-1H-1,2,3-triazole-4-carboxylic acid in 250 ml of liquid ammonia at −78° C., 7.2 g (312 mmoles) of sodium pellets were added, in portions, until the solution maintained a dark blue color. The reaction was then quenched, with 10 g (128 mmoles) of ammonium carbonate. The resulting yellow mixture was allowed to warm to room temperature and the ammonia evaporated. The solid residue was dissolved in 70 ml of water and extracted with ether. The aqueous phase was then adjusted to pH 1 with 12N hydrochloric acid and 140.0 g (95%) of 5-ethyl-1H-1,2,3-triazole-4-carboxylic acid was precipitated as a yellow solid. The structure was confirmed by n.m.r. and I.R.

EXAMPLE 7

Ethyl-1H-1,2,3-triazole

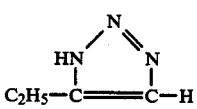

A 6.44 g (45.7 mmole) sample of 5-ethyl-1H-1,2,3-triazole-4-carboxylic acid was heated to 195° C. and held at that temperature until the evolution of carbon dioxide had ceased. The residual oil was cooled and dissolved in 100 ml of a 50% acetone/chloroform solution. This mixture was dried over anhydrous magnesium sulfate, then treated with decolorizing carbon and filtered. Concentration in vacuo gave 3.9 g (89%) of 4-ethyl-1H-1,2,3-triazole as a golden oil. The structure was confirmed by n.m.r. and I.R.

EXAMPLE 8

4-Bromo-5-ethyl-1H-1,2,3-triazole

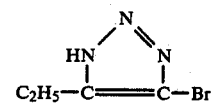

To a solution of 1.84 g (19 mmoles) of 4-ethyl-1H-1,2,3-triazole and 2.0 g (50 mmoles) of sodium hydroxide in 25 ml of water at 0° C. was added 3.0 g (19 mmoles) of bromine by drop. The reaction mixture was warmed to room temperature and stirred overnight. The aqueous solution was acidified to pH 2 with 12N hydrochloric acid and extracted with dichloromethane. The organic phase was washed with brine and dried over anhydrous sodium sulfate. Concentration in vacuo gave 2.3 g (69%) of 4-bromo-5-ethyl-1H-1,2,3-triazole as a yellow oil. The structure was confirmed by n.m.r. and I.R.

The following is a table of certain selected compounds that are preparable according to the procedure described herein. Compound numbers assigned to each compound are used throughout the remainder of the application.

TABLE I

| Compound Number | X | Y | $R^1$ | $R^2$ |
|---|---|---|---|---|
| 1 | Br | Br | $CH_3$ | $CH_3$ |
| 2 | Br | Br | $C_2H_5$ | $C_2H_5$ |
| 3 | Br | Br | $-(CH_2)_4-$ | |
| 4 | Br | Br | $n-C_3H_7$ | $n-C_3H_7$ |
| 5 | Br | Br | $i-C_4H_9$ | $i-C_4H_9$ |
| 6 | Br | phenyl | $CH_3$ | $CH_3$ |
| 7 | Br | $CH_3$ | $CH_3$ | $CH_3$ |
| 8 | Br | $C_2H_5$ | $CH_3$ | $CH_3$ |
| 9 | Br | $i-C_3H_7$ | $CH_3$ | $CH_3$ |
| 10 | H | $c-C_5H_9$ | $C_2H_5$ | $C_2H_5$ |
| 11 | H | Br | $CH_3$ | $CH_3$ |
| 12 | H | phenyl | $n-C_3H_7$ | $n-C_3H_7$ |
| 13 | H | $n-C_3H_7$ | $n-C_3H_7$ | $n-C_3H_7$ |
| 14 | H | $C_2H_5$ | $CH_3$ | $CH_3$ |
| 15 | H | $i-C_3H_7$ | $CH_3$ | $CH_3$ |
| 16 | H | $n-C_3H_7$ | $CH_3$ | $CH_3$ |
| 17 | H | $sec-C_4H_9$ | $CH_3$ | $CH_3$ |
| 18 | H | $CH_3$ | $CH_3$ | $CH_3$ |
| 19 | H | $sec-C_4H_9$ | $n-C_3H_7$ | $n-C_3H_7$ |
| 20 | H | $C-C_5H_9$ | $CH_3$ | $CH_3$ |
| 21 | Br | Br | $-(CH_2)_{5ab,4}-$ | |
| 22 | Br | Br | $-(CH_2)_6-$ | |

TABLE I-continued

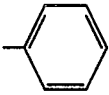

| Compound Number | X | Y | R¹ | R² |
|---|---|---|---|---|
| 23 | Br | phenyl | CH₃ | CH₃O |

Herbicidal Screening Tests

As previously mentioned, the herein described compounds produced in the above-described manner are phytotoxic compounds which are useful and valuable in controlling various plant species. Selected compounds of this invention were tested as herbicides in the following manner.

Pre-emergence herbicide test. On the day preceding treatment, seeds of eight different weed species are planted in loamy sand soil in individual rows using one species per row across the width of a flat. The seeds used are green foxtail (FT) (*Setaria viridis*), watergrass (WG) (*Echinochloa crusgalli*), wild oat (WO) (*Avena fatua*), annual morningglory (AMG) (*Ipomoea lacunosa*), velvetleaf (VL) (*Abutilon theophrasti*), Indian mustard (MD) (*Brassica juncea*), curly lock (CD) (*Rumex crispus*), and yellow nutsedge (YNG) (*Cyperus esculentus*). Ample seeds are planted to give about 20 to 40 seedlings per row, after emergence, depending upon the size of the plants.

Using an analytical balance, 600 milligrams (mg) of the compound to be tested are weighed out on a piece of glassine weighing paper. The paper and compound are placed in a 60 milliiter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 Kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the tests are shown in the following Table II.

TABLE II

Pre-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1 | 100 | 97 | 97 | 50 | 70 | 90 | 0 | 15 |
| 2 | 100 | 100 | 30 | 0 | 100 | 100 | 100 | 100 |
| 3 | 100 | 100 | 30 | 0 | 0 | 100 | 100 | 0 |
| 4 | 100 | 100 | 90 | 0 | 0 | 35 | 100 | 0 |
| 5 | 100 | 100 | 90 | 0 | 0 | 20 | 30 | 0 |
| 6 | 100 | 100 | 0 | 0 | 0 | 0 | 0 | 0 |
| 7 | 100 | 95 | 35 | 30 | 0 | 45 | 100 | 40 |
| 8 | 95 | 95 | 30 | 0 | 0 | 0 | 80 | 99 |
| 9 | 100 | 100 | 0 | 0 | 0 | 100 | 90 | 100 |
| 10 | 90 | 85 | 30 | 0 | 0 | 0 | 0 | 0 |
| 12 | 95 | 98 | 0 | 0 | 0 | 0 | 0 | 0 |
| 13 | 90 | 85 | 0 | 0 | 0 | 0 | 75 | 0 |
| 14 | 80 | 25 | 0 | 0 | 0 | 0 | 75 | 0 |
| 15 | 25 | 25 | 10 | 0 | 0 | 0 | 80 | 0 |
| 16 | 25 | 50 | 0 | 0 | 0 | 0 | 80 | 0 |
| 17 | 90 | 80 | 25 | 0 | 0 | 80 | 80 | 20 |
| 19 | 95 | 95 | 0 | 0 | 0 | 0 | 50 | 0 |
| 20 | 50 | 50 | 0 | 0 | 0 | 0 | 60 | 0 |
| 21 | 80 | 80 | 25 | 0 | 0 | 60 | 0 | — |
| 22 | 100 | 100 | 60 | 25 | 90 | 85 | 90 | 70 |
| 23 | 100 | 100 | 75 | 0 | 0 | 35 | 35 | 0 |

— = Not tested.

Post-Emergence Herbicide Test: This test is conducted in an identical manner to the testing procedure for the pre-emergence herbicide text, except the seeds of the eight different weed species are planted 10-12 days before treatment. Also, watering of the treated flats is confined to the soil surface and not to the foliage of the sprouted plants.

The results of the post-emergence herbicide test are reported in Table III.

TABLE III

Post-Emergence Herbicidal Activity
Application Rate - 4.48 kg/ha

| Cmpd. No. | FT | WG | WO | AMG | VL | MD | CD | YNG |
|---|---|---|---|---|---|---|---|---|
| 1 | 90 | 40 | 0 | 40 | 40 | 50 | 40 | 20 |
| 2 | 70 | 75 | 30 | 0 | 0 | 40 | 0 | 80 |
| 3 | 80 | 70 | 60 | 20 | 70 | 100 | 0 | 60 |
| 4 | 70 | 70 | 15 | 15 | 50 | 50 | 100 | 0 |
| 5 | 50 | 40 | 0 | 0 | 0 | 0 | 0 | 0 |
| 6 | 80 | 40 | 20 | 90 | 0 | 100 | 0 | 0 |
| 7 | 10 | 10 | 15 | 20 | 15 | 100 | 10 | 15 |
| 8 | 0 | 0 | 0 | 10 | 80 | 100 | 0 | 0 |
| 9 | 40 | 45 | 0 | 0 | 50 | 100 | 0 | 0 |
| 10 | 0 | 0 | 0 | 40 | 0 | 75 | 0 | 0 |
| 12 | 0 | 15 | 0 | 15 | 30 | 70 | 0 | 0 |
| 13 | 0 | 0 | 0 | 30 | 0 | 0 | 60 | 0 |
| 14 | 80 | 0 | 0 | 0 | 0 | 0 | 60 | 0 |
| 15 | 25 | 0 | 0 | 25 | 0 | 5 | 0 | 0 |
| 16 | 90 | 0 | 0 | 25 | 15 | 15 | 0 | 0 |
| 17 | 0 | 0 | 0 | 20 | 0 | 0 | 0 | 0 |
| 19 | 0 | 0 | 0 | 20 | 0 | 0 | 60 | 0 |
| 20 | 0 | 0 | 0 | 0 | 0 | 0 | 20 | 0 |
| 21 | 50 | 10 | 0 | 0 | 0 | 30 | 40 | 25 |
| 22 | 0 | 0 | 0 | 65 | 100 | 80 | 0 | — |
| 23 | 85 | 85 | 10 | 90 | 40 | 100 | 40 | 0 |

— = Not tested.

The compounds of the present invention are useful as herbicides, and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such as wetting agents, dispersing agents or emulsifiers; oil such as heavy aromatic naphthas, kerosene or other petroleum fractions, or vegetable oils; and/or stickers such as dextrins, glue or synthetic resins.

Typical wetting, dispersing, or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the herbicidal composition.

Dusts, which are free-flowing admixtures of the active ingredients with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of powder-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the composition into the soil as the water is absorbed therein. Dust compositions, granular compositions or liquid formulations applied to the surface of the soil can be distributed below the surface of the soil by conventional means such as discing, dragging or mixing operations.

We claim:

1. A compound having the structural formula

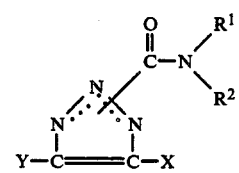

wherein X is hydrogen or bromine; Y is bromine, phenyl, $C_1$–$C_4$ alkyl or $C_4$–$C_6$ cycloalkyl; $R^1$ and $R^2$ independently are $C_1$–$C_6$ or, $C_1$–$C_4$ alkoxy, or $R^1$ and $R^2$ together form a ring with the nitrogen to which they are attached having 3–8 carbon atoms, optionally substituted with one or two methyl groups.

2. The compound of claim 1 wherein X is bromine, Y is bromine, $R^1$ is $C_1$–$C_6$ alkyl and $R^2$ is $C_1$–$C_6$ alkyl or $R^1$ and $R^2$ are $C_3$–$C_8$ alkylene.

3. The compound of claim 1 wherein X is bromine, Y is bromine, $R^1$ is $C_1$–$C_4$ alkyl and $R^2$ is $C_1$–$C_4$ alkyl.

4. The compound of claim 1 wherein X is bromine, Y is bromine, $R^1$ is methyl and $R^2$ is methyl.

5. The compound of claim 1 wherein X is bromine, Y is bromine, $R^1$ is ethyl and $R^2$ is ethyl.

6. The compound of claim 1 wherein X is bromine, Y is bromine and $R^1$ and $R^2$ together are butylene.

7. The compound of claim 1 wherein X is bromine, Y is bromine, $R^1$ is n-propyl and $R^2$ is n-propyl.

8. The compound of claim 1 wherein X is bromine, Y is methyl, $R^1$ is methyl and $R^2$ is methyl.

9. The compound of claim 1 wherein Y is bromine, Y is bromine, and $R^1$ and $R^2$ together are hexylene.

10. The compound of claim 1 wherein X is bromine, Y is isopropyl, $R^1$ is methyl and $R^1$ is methyl.

11. The method of controlling undesirable vegetation comprising applying to the area where control is desired an herbicidally effective amount of a compound having the structural formula

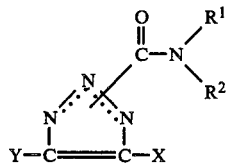

wherein X is hydrogen or bromine; Y is bromine, phenyl, $C_1$-$C_4$ alkyl or $C_4$-$C_6$ cycloalkyl; $R^1$ and $R^2$ independently are $C_1$-$C_6$ or $C_1$-$C_4$ alkoxy, or $R^1$ and $R^2$ together form a ring with the nitrogen to which they are attached having 3-8 carbon atoms, optionally substituted with one or two methyl groups.

12. The method of claim 11 wherein X is bromine, Y is bromine, $R^1$ is $C_1$-$C_6$ alkyl and $R^2$ is $C_1$-$C_6$ alkyl or $R^1$ and $R^2$ are $C_3$-$C_8$ alkylene.

13. The method of claim 11 wherein X is bromine, Y is bromine, $R^1$ is $C_1$-$C_4$ alkyl and $R^2$ is $C_1$-$C_4$ alkyl.

14. The method of claim 11 wherein X is bromine, Y is bromine, $R^1$ is methyl and $R^2$ is methyl.

15. The method of claim 11 wherein X is bromine, Y is bromine, $R^1$ is ethyl and $R^2$ is ethyl.

16. The method of claim 11 wherein X is bromine, Y is bromine and $R^1$ and $R^2$ together are butylene.

17. The method of claim 11 wherein X is bromine, Y is bromine, $R^1$ is n-propyl and $R^2$ is n-propyl.

18. The method of claim 11 wherein X is bromine, Y is methyl, $R^1$ is methyl and $R^2$ is methyl.

19. The method of claim 11 wherein Y is bromine, Y is bromine, and $R^1$ and $R^2$ together are hexylene.

20. The method of claim 11 wherein X is bromine, Y is isopropyl, $R^1$ is methyl and $R^1$ is methyl.

* * * * *